United States Patent
Delie et al.

(10) Patent No.: US 10,363,227 B2
(45) Date of Patent: Jul. 30, 2019

(54) PHARMACEUTICAL FORMULATION FOR USE IN THE TREATMENT AND/OR PREVENTION OF RESTENOSIS

(71) Applicant: Centre Hospitalier Universitaire Vaudois (C.H.U.V.), Lausanne (CH)

(72) Inventors: Florence Delie, Petit-Lancy (CH); Olivier Jordan, Prangins (CH); Ludmila Luca, Goldiwil (CH); François Saucy, Lausanne (CH); Jacques-Antoine Haefliger, Lausanne (CH); Ioanna Mylonaki, Genève (CH)

(73) Assignee: Centre Hospitalier Universitaire Vaudois, Lausanne (CH)

(*) Notice: Subject to any disclaimer, the term of this patent is extended or adjusted under 35 U.S.C. 154(b) by 0 days.

(21) Appl. No.: 14/779,985

(22) PCT Filed: Mar. 27, 2014

(86) PCT No.: PCT/EP2014/056157
§ 371 (c)(1),
(2) Date: Sep. 25, 2015

(87) PCT Pub. No.: WO2014/154804
PCT Pub. Date: Oct. 2, 2014

(65) Prior Publication Data
US 2016/0045450 A1    Feb. 18, 2016

Related U.S. Application Data

(60) Provisional application No. 61/805,716, filed on Mar. 27, 2013.

(51) Int. Cl.
*A61K 9/50*    (2006.01)
*A61L 31/16*   (2006.01)
(Continued)

(52) U.S. Cl.
CPC .......... *A61K 9/5084* (2013.01); *A61K 9/0024* (2013.01); *A61K 9/06* (2013.01);
(Continued)

(58) Field of Classification Search
None
See application file for complete search history.

(56) References Cited

U.S. PATENT DOCUMENTS 5,645,592 A * 7/1997 Nicolais .............. A61L 31/10
606/63
7,534,448 B2 * 5/2009 Saltzman ............. A61K 9/0019
424/417
(Continued)

FOREIGN PATENT DOCUMENTS

CA       2445524 A1 * 11/2002 ............... A61F 2/91
WO   WO-2001/054748 A1    8/2001
WO   WO-2007009698 A1 *  1/2007 ......... A61K 31/4155

OTHER PUBLICATIONS

Fukuda et al. (Fluvastatin accelerates re-endothelialization impaired by local sirolimus treatment, European Journal of Pharmacology 612 (2009) 87-92).*

(Continued)

*Primary Examiner* — Robert A Wax
*Assistant Examiner* — Melissa S Mercier
(74) *Attorney, Agent, or Firm* — Harness Dickey & Pierce P.L.C.

(57) ABSTRACT

The present invention relates generally to a pharmaceutical formulation for use in the treatment and/or prevention of restenosis in a subject in need thereof. Methods of treatment and/or prevention are also provided.

9 Claims, 10 Drawing Sheets

(51) Int. Cl.
| | | |
|---|---|---|
| *A61K 9/00* | (2006.01) | |
| *A61K 9/06* | (2006.01) | |
| *A61K 47/36* | (2006.01) | |
| *A61K 9/16* | (2006.01) | |
| *A61L 31/04* | (2006.01) | |
| *A61L 31/14* | (2006.01) | |
| *A61K 31/132* | (2006.01) | |
| *A61K 31/22* | (2006.01) | |
| *A61K 31/366* | (2006.01) | |
| *A61K 31/405* | (2006.01) | |
| *A61K 31/47* | (2006.01) | |
| *A61K 31/60* | (2006.01) | |
| *A61K 31/65* | (2006.01) | |
| *A61K 31/337* | (2006.01) | |
| *A61K 31/40* | (2006.01) | |
| *A61K 31/616* | (2006.01) | |

(52) U.S. Cl.
CPC .......... *A61K 9/1647* (2013.01); *A61K 31/132* (2013.01); *A61K 31/22* (2013.01); *A61K 31/337* (2013.01); *A61K 31/366* (2013.01); *A61K 31/40* (2013.01); *A61K 31/405* (2013.01); *A61K 31/47* (2013.01); *A61K 31/60* (2013.01); *A61K 31/616* (2013.01); *A61K 31/65* (2013.01); *A61K 47/36* (2013.01); *A61L 31/042* (2013.01); *A61L 31/145* (2013.01); *A61L 31/16* (2013.01); *A61L 2300/416* (2013.01); *A61L 2300/422* (2013.01)

(56) References Cited

U.S. PATENT DOCUMENTS

| 9,308,190 B2* | 4/2016 | Li | A61K 31/22 |
|---|---|---|---|
| 2003/0008971 A1* | 1/2003 | Won | A61K 9/205 |
| | | | 525/54.2 |
| 2004/0018228 A1* | 1/2004 | Fischell | A61B 17/06166 |
| | | | 424/450 |

OTHER PUBLICATIONS

International Preliminary Report on Patentability dated Jul. 29, 2015 issued in PCT Patent Application No. PCT/EP2014/056157.
International Search Report and Written Opinion dated Aug. 1, 2014 issued in PCT Patent Application No. PCT/EP2014/056157.
Masaki, T., et al. (2004), "Inhibition of neointimal hyperplasia in vascular grafts by sustained perivascular delivery of paclitaxel", *Kidney International*, 66: 2061-2069.
Torsney, E., et al. (2004), "Thrombosis and Neointima Formation in Vein Grafts Are Inhibited by Locally Applied Aspirin Through Endothelial Protection", *Circ Res.*, 94: 1466-1473.
Wiedemann, D., et al. (2012) "Perivascular administration of drugs and genes as a means of reducing vein graft failure", *Current Opinion in Pharmacology*, 12: 203-216.
Zhang, L., et al. (2012), "Local Delivery of Pravastatin Inhibits Intimal Formation in a Mouse Vein Graft Model", *Canadian Journal of Cardiology*, 28: 750-757.
Dubuis C., et al., (2013) "Atorvastatin-Loaded Hydrogel Affects the Smooth Muscle Cells of Human Veins", J Pharmacol Exp Ther 347:574-581.
Jaschke B., et al., (2005) "Local Statin therapy Differentially Interferes with Smooth Muscle and Endothelial Cell Proliferation and Reduces Neointima on a Drug-Eluting Stent Platform" Cardiovascular Research 68:483-492.
Miyauchi K., et al., (2008) "Effectiveness of Statin-Eluting Stent on Early Inflammatory Response and Neointimal Thickness in a Porcine Coronary Model", Circulation Journal, 72:832-838.
Moon M., et al., (2004) "Perivascular Delivery of Losartan with Surgical Fibrin Glue Prevents Neointimal Hyperplasia after Arterial Injury", Journal of Vascular Surgery, 40:1, 130-137.
Mylonaki I., et al., (2016) "Perivascular Sustained Release of Atorvastatin from a Hydrogel-Microparticle Delivery System Decreases Intimal Hyperplasia" Journal of Controlled Release, 232:93-102.
Mylonaki I., et al., (2018) "Evaluating Intimal Hyperplasia Under Clinical Conditions", Interactive CardioVascular and Thoracic Surgery, 1-10.
Park K., (2016) "Perivascular Administration: The Outside-In Concept" Journal of Controlled Release, 232:265.
Simons M., et al., (1992) "Antisense c-myb Oligonucleotides Inhibit Intimal Arterial Smooth Muscle Cell Accumulation in Vivo" Letters to Nature, 359:67-70.

* cited by examiner

Upper panel

Lower panel

PHARMACEUTICAL FORMULATION FOR USE IN THE TREATMENT AND/OR PREVENTION OF RESTENOSIS

PRIORITY STATEMENT

This application is a national stage application under 35 U.S.C. § 371 of PCT International Application No. PCT/EP2014/056157, which has an international filing date of 27 Mar. 2014 and which claims the benefit of U.S. Provisional Application 61/805,716 filed 27 Mar. 2013. The contents of each application recited above are incorporated herein by reference in their entirety.

FIELD OF THE INVENTION

The present invention relates generally to pharmaceutical formulations for use in the treatment and/or prevention of restenosis in a subject in need thereof. Methods of treatment and/or prevention are also provided.

BACKGROUND OF THE INVENTION

Open surgical revascularization defined as the improvement of blood supply to a body part or organ using a graft is performed in over 30 Mio patients around the world each year. Unfortunately, graft failure occurs in 20 to 50% of the cases within 5 years, mainly due to stenosis at the anastomosis site leading to occlusion [1].

In the case of endovascular intervention, medical devices have been identified to prevent intraluminal vessel stenosis such as stents or plain balloon with promising results. However, when open revascularization is mandatory, no platform is available for local drug delivery. Current post-open revascularization treatments imply repetitive oral dosing of the active compound(s) with the risk of side effects.

To increase the chance of reperfusion by avoiding the development of stenosis, a local preventive treatment applied at the site of the surgery would be safer and more efficient than systemic administration. To be efficient a local therapy needs to stay located at the site of administration and to deliver the drug(s) according to an optimal time schedule defined by the development of the pathology. This formulation needs also to be biocompatible and biodegradable to be eliminated via either hydrolysis or enzymolysis to avoid a second surgery to remove the drug delivery device. Furthermore, it should be delivered in a small volume, about 5 ml for humans and should not damage the graft or the surrounding tissues.

Even though the perivascular route of administration has been tested in animal models, the success of this approach has been limited. To date, no clinical application is yet available in the market. The reasons for this limited success lies in feasibility restrictions. So far, no formulation achieved long term local permanence at the diseased site, combined with optimal drug(s) release profile(s) fitting the development of the pathology, using biocompatible and biodegradable polymers for the preventive treatment of restenosis after open surgical revascularization.

These goals have been attained in the present invention by providing pharmaceutical formulations for use in the treatment and/or prevention of restenosis in a subject in need thereof in accordance with the present invention.

DESCRIPTION OF THE FIGURES

FIG. 1: Schematic representation of the invention with optimal release kinetic profile according to the development of IH. A rapidly delivered compound of the invention effective on the acute inflammatory phase, or any active metabolite thereof, will be loaded into the hydrogel and released during the early phase of the development of the restenosis. The hydrogel, due to its inherent viscosity, will ensure the localization of the drug delivery system for the time needed. A second compound of the invention, or any active metabolite thereof, loaded in the microspheres active on the late phase of the restenosis, will be released in a sustained manner, in this figure for example for up to 4 weeks.

FIG. 4: The hydrogel incorporating ATV decreased the migration of hVSMCs Upper panel: Primary hVSMCs migration rate was assessed using silicon culture inserts defining a cell free gap ~500 µm (lines). hVSMCs grown under control conditions (control medium) migrated into this gap to fill it in about 48 h. This migration was decreased by 5 and 10 µM ATV, whether the drug was added directly to the medium (ATV medium) or was released by the hydrogel (ATV gel). Bar represents 80 µm. Lower panel: Inhibition of cell migration was observed at 36 h in the presence of 5 µM ATV, and already at 24 h in the presence of 10 µM ATV directly added to the culture medium (left panel). A similar inhibition of hVSMCs migration was observed using the ATV-loaded hydrogel (right panel). *P<0.05, **P<0.01 versus control cells incubated in the absence of ATV.

FIG. 5: The hydrogel incorporating ATV decreases transmigration. Upper panel: Transmigration of hVSMCs in presence or absence of ATV was assessed with the modified Boyden chamber technique. Lower panel: Quantitative assessment of the transmigrated cells demonstrate a significant decrease in the capacity of hVSMCs to transmigrate in presence of ATV in medium or released from the hydrogel. *P<0.05, P<0.01 and *P<0.001 versus control cells incubated in absence of ATV. Bar represents 20 µm.

FIG. 6: Analysis of transcripts and proteins of hVSMC. Measurements of various mRNAs levels in hVSMCs in presence of ATV directly added in the medium were performed. PAI-1 and MMP2 and Cx43 mRNA levels were decreased whereas tPA and HMOX transcripts were increased after 24 hours incubation. No significant change was observed when ATV was released from the hydrogel at 24 h. In contrast, a similar regulation of the tested genes was observed in presence of ATV released from the hydrogel after 48 hours. *P<0.05, P<0.01 and *P<0.001 versus cells incubated without ATV (Control).

FIG. 9: The development of intimal hyperplasia (IH) decreases in presence of ATV loaded particles and/or free ATV incorporated in the hydrogel. Upper panel: Photomicrographs (Verhoeff-van Gieson elastin staining) of representative cross-sections from carotid arteries of WT mice submitted to the CAL model (magnification ×10). Untreated mice were used as control. All treated mice received a total constant ATV concentration of 1 mM either in hydrogel (G) and/or microspheres (M) loaded (+) or not (−) for example, in the G+M+ condition, G+=500 μM and M+=500 μM whereas in the condition G−M+, G−: 0 mM and M+=1 mM). Middle panel: preliminary results show that, compared to WT control mice, at Day 14 and Day 28 after surgery, the intima thickness is markedly decreased in the animals treated with ATV-loaded microspheres. Lower panel: Quantitative assessment of the Intima/Media ratio (I/M) shown for different distances from the ligation site at 14 days (left panel) and 28 days (right panel) demonstrates that, compared to controls, the intima/media ratio of the ligated carotids was decreased at 0.5, 1, 1.5 and 2 mm from the ligation 14 and 28 days after ligation in presence of ATV-loaded microspheres 1 mM.

SUMMARY OF THE INVENTION

The present invention provides pharmaceutical formulations for use in the treatment and/or prevention of restenosis in a subject in need thereof, said pharmaceutical formulations consisting in a gel phase comprising
i) at least one rapidly delivered compound effective on the acute inflammatory phase, or any active metabolite of said at least one compound, and
ii) a sustained release formulation comprising at least one compound, or any active metabolite of said at least one compound, effective on later phases of restenosis development.

Also disclosed is a method of treatment and/or prevention of restenosis in a subject in need thereof, said method comprising administering a pharmaceutical formulation consisting in a gel phase comprising i) at least one rapidly delivered compound effective on the acute inflammatory phase, or any active metabolite of said at least one compound, and ii) a sustained release formulation comprising at least one compound effective on later phases of restenosis development.

The invention further provides a kit for the treatment and/or prevention of restenosis comprising a pharmaceutical formulation for use in the treatment and/or prevention of restenosis in a subject in need thereof, said pharmaceutical formulation consisting in a gel phase comprising i) at least one rapidly delivered compound effective on the acute inflammatory phase, or any active metabolite of said at least one compound, and ii) a sustained release formulation comprising at least one compound, or any active metabolite of said at least one compound, effective on later phases of restenosis development.

DESCRIPTION

The hyperacute stage is initiated by injury of an existing genuine intimal lining. Proliferation of hVSMCs (human vascular smooth muscle cells) is set in through two mechanisms comprising damaged endothelial cells and hVSMC proliferation. The acute stage is characterized by the organization of the thrombus, endothelial cell ingrowth and the release of growth factors. In this stage, hours to weeks after injury, the integrity of the extracellular matrix (ECM) is affected, which stimulates hVSMCs migration from the media to the intima [2]. In the third and final chronic stage of intimal hyperplasia (IH), new ECM is synthesized, a process that may continue for months after the initial lesion [3].

In the first 24 h, vein grafts undergo a period of ischemia followed by reperfusion, resulting in the generation of superoxide and other reactive oxygen species that trigger cytotoxicity of endothelial and hVSMCs [4]. Once in the intima, the hVSMCs proliferate at an amplified rate and settle on newly synthesized ECM, thereby contributing further to the intimal thickening [5]. The surgical preparation of saphenous veins for the surgery causes considerable removal of the endothelium [6]. Endothelial denudation allows platelet and leukocyte adhesion immediately after graft implantation that precipitates thrombosis, as well as acting as an initiating factor for intimal thickening [7-9]. Activated hVSMCs are more synthetic and have higher proliferation and migration rates [10]. As a result, hVSMCs migrate from the media into the intima where they proliferate and secrete ECM, leading to the thickening of the intimal layer. Moreover, coagulation factors and fibrinolysis products contribute actively to hVSMC activation and intimal thickening [11]. Enhanced leukocyte binding is enabled due to increased adhesion molecule expression within the vein graft after implantation [12]. Adherent leukocytes, particularly neutrophils, release numerous pro-inflammatory substances, including leukotrienes, interleukins, histamine, tumor necrosis factor, platelet activating factor and proteases, all of which promote hVSMCs proliferation and migration [13]. Monocyte adhesion also occurs early after vein graft implantation and promotes intimal thickening. Monocytes invade into the intima and differentiate into resident macrophages and then the foam cells, after uptake of lipid, which are a major contributor to atherogenesis. Endothelial denudation also results in the loss of vasculoprotective systems principally nitric oxide (NO) and prostacyclin as well as heparin-like substances that inhibit thrombosis and inflammation [14].

The blood vessel wall is a highly organized structure of cells and ECM [15]. To enable hVSMCs migration and proliferation the ECM and cadherin contacts must be digested by proteases including MMPs. Furthermore direct proof of the involvement of MMPs in vein graft IH has been provided by the observation that overexpression of the endogenous MMP inhibitors, tissue inhibitors of MMPs (TIMPs) significantly retarded intimal thickening [16].

The present invention thus relates to a pharmaceutical formulation for use in the treatment and/or prevention of restenosis in a subject in need thereof, said pharmaceutical formulation consisting in a gel phase comprising i) at least one rapidly delivered compound effective on the acute inflammatory phase, or any active metabolite of said at least one compound, and ii) a sustained release formulation comprising at least one compound, or any active metabolite of said at least one compound, effective on later phases of restenosis development.

As used herein, "restenosis" or "stenosis" refers to the post interventional recurrence of narrowing generally in an artery or vein. The degree of narrowing is inconstant but significant when over 70% of the vessel lumen diameter is occluded. Restenosis occurs in 20-50% of patients after balloon angioplasty and in 10-30% of patients receiving a stent.

The "acute inflammatory phase of the early stage of restenosis development" This phase is followed by a late stage characterized by the deposit of ECM in the subintimal layer leading to increase the thickness of the wall with subsequent decrease of the vessel lumen.

As used herein, the "acute inflammatory phase of the early stage of restenosis development" refers to the initial phase represented by the accumulation in the vessel wall of macrophages. Additionally, monocytes with cytokines trigger the hVSMC migration through the extracellular matrix.

This early stage is followed by a "later phase of restenosis" as used herein. This "later phase of restenosis" characterized by the deposit of extracellular matrix in the subintimal layer leading to increase the thickness of the wall with subsequent decrease of the vessel lumen.

As used herein, the "gel phase" refers to different types of gels that have been described in the art. Although, numerous studies relate the use of hydrogels, for perivascular administration; so far, no project has gone to clinical study. Failure is due to the rapid degradation, or washing of, of the hydrogel, leading to a fast release kinetics profile. Alternatively or additionally, the gels of the invention can be thermosensitive, meaning that they are liquid at temperature below body temperature and harden above 30° C.

Thus, the gel phase of the pharmaceutical formulation of the invention is selected from the non-limiting group comprising hydrogel based on biopolymers such as hyaluronic acid, alginate, chitosan or synthetic polymers such as poloxamers or thermosensisitve triblock PLGA-PEG polymers. Preferably, said hydrogel consists in hyaluronic acid, or of one of its salts.

Alternatively, said hyaluronic acid, or one of its salts, is cross-linked or essentially cross-linked.

Hyaluronic acid is a natural polymer of disaccharides, D-glucuronic acid and D-N-acetylglucosamine, linked via alternating β-1,4 and β-1,3 glycosidic bonds. It is widely distributed throughout connective, epithelial, and neural tissues. Therefore, the polymer, by its natural properties, may also contribute to the drug delivery system efficacy.

Any commercially available hyaluronic acid or salt of said hyaluronic acid may be selected for the gel phase of the pharmaceutical formulation. A typical example of commercially available hyaluronic acid is Fortelis Extra® (Anteis).

Preferably, the at least one rapidly delivered compound is a drug effective on the hyperacute stage of the restenosis that can be incorporated in the gel in solution. The gels are then freeze-dried and the lyophilized hydrogels are rehydrated with water before use. Any other technique known in the art can also be applied.

Combinatory drug therapy as a treatment of restenosis is appealing, if two or more drugs with different and potentially synergistic effects can be combined. To have a powerful combined effect on restenosis, a specific drug should inhibit early inflammatory events whereas another one should inhibit IH. A controlled local drug delivery to the adventitia or drugs that discriminate vascular cell types may be critical in selective modification of vessel wall geometry.

Usually, the at least one rapidly delivered compound is effective on the acute inflammatory phase of the early stage of restenosis development and is selected from the group comprising a non-steroidal anti-inflammatory drugs (such as aspirin or nitroaspirin), anticonverting enzyme inhibitor, chymase inhibitor, suramin, methylaminochroman, superoxide dismutase, L arginin, spermine/NO, marimastat, doxycyclin, calcium channel blocker, perillyl alcohol, BSF 302146 (ETA), and L-158,809 (angiotensin II), or a combination of two or more of these compounds. Most preferably, the at least one rapidly delivered compound is aspirin.

Alternatively, the at least one rapidly delivered compound is a drug effective on the hyperacute stage of the restenosis and may be selected among the non-limiting group of statins such as atorvastatin, fluvastatin, pravastatin and simvastatin or a combination of two or more thereof.

Usually, the sustained release formulation is in the form of microspheres. Preferably said sustained release formulation is in the form of microspheres made of a biocompatible, biodegradable polymer. Said biocompatible, biodegradable polymer is selected from the non-limiting group comprising a polylactide, a copolymer of a polylactide, a polyglycolide, a copolymer of a polyglycolide, a poly(lactide-co-glycolide) copolymer, a polylactic acid, a copolymer of a polylactic acid, a polyglycolic acid, a copolymer of a polyglycolic acid, a poly(lactic acid-co-glycolic acid) copolymer, a polycaprolactone, a copolymer of a polycaprolactone, a polycarbonate, a copolymer of a polycarbonate, a polyesteramide, a copolymer of a polyesteramide, a polyanhydride, a copolymer of a polyanhydride, a polyamino acid, a copolymer of a polyamino acid, a polyorthoester, a copolymer of a polyorthoester, a polycyanoacrylate, a copolymer of a polycyanoacrylate, a poly(p-dioxanone), a copolymer of a poly(p-dioxanone), a polyalkylene oxalate, a copolymer of a polyalkylene oxalate, a polyurethane, a copolymer of a polyurethane, or a combination of two or more thereof.

Several formulations using the microsphere technology are already available on the market, for instance Lupron Depot®, Decapeptyl®, Somatulin® LA, and Risperidal® Consta™. Microspheres may be developed with different polymers and preparation methods. Thus, the release rate of the loaded drug may be controlled by several parameters including the nature and the molecular weight of the polymer, the size of the particles, the presence of specific excipients. Amongst the polymers used for microencapsulation, polylactic acid (PLA) and polylactic-co-glycolic acid (PLGA) stay the most preferred. These polymers are well tolerated, biodegradable with the release of lactic and glycolic acids which are eliminated via the Krebs' cycle. Furthermore, drug formulations containing such polymers; have been approved for human use by the American Food and Drug Administration (US-FDA).

Usually, the sustained release formulation sustains a controlled and stable release of the at least one compound effective on later phases of restenosis development for a time sufficient to revert the phenotype of altered hVSMCs.

Any other microparticle suitable for the delivery of a drug for the perivascular administration is envisioned. For example, Edelman et al. developed a delivery system for basic fibroblast growth factor where the protein is adsorbed on heparin-sepharose beads before encapsulation in calcium alginate microcapsules that were directly placed adjacent to the arteries [17].

Preferably, the mean size of the microparticles, e.g. the microspheres or nanospheres is between 0.1 µm to 300 µm, more preferably between 5 µm to 40 µm, even more preferably between 14 µm to 20 µm.

Preferably also, the at least one compound effective on later phases of restenosis is loaded on microspheres prepared, e.g. according to an emulsification-evaporation process. A solution of Resomer RG502 and the at least one compound effective on later phases of restenosis was prepared in methylene chloride and vigorously mixed with an aqueous solution of polyvinyl alcohol. The emulsion was then added in a large volume of water and the solvent was left to evaporate at room temperature overnight. Particles were washed and concentrated by successive steps of centrifugation/resuspension before freeze-drying. Alternatively, particles can be characterized for size, morphology and the at least one compound effective on later phases of restenosis loading efficiency can be determined by a HPLC method. They are then incorporated in the gel by gentle mixing until a homogeneous suspension was obtained. Any other method for preparing the at least one compound effective on later phases of restenosis loaded microspheres or particles can be used.

Usually also, the at least one compound effective on later phases of stenosis development is selected from the group comprising a 3-hydroxy-3-methylglutaryl-CoA reductase inhibitor, a mitotic inhibitor, or a combination of two or more thereof.

Preferably, the 3-hydroxy-3-methylglutaryl-CoA reductase inhibitor is a statin, a pharmaceutically acceptable salt or ester thereof. Statins are a class of drugs used to lower cholesterol levels by competitively inhibiting the enzyme HMG-CoA reductase, which plays a central role in the production of cholesterol in the liver.

In case the at least one compound effective on later phases of restenosis development is a statin, a pharmaceutically acceptable salt or ester thereof, then it is selected from the group comprising atorvastatin, fluvastatin, pravastatin, and simvastatin, or a combination of two or more thereof. Most preferably, the statin is atorvastatin (ATV), a pharmaceutically acceptable salt or ester thereof.

Preferably also, the amount of drug loaded per mg of particles or microsphere will depend on the drug itself. For example, in case the statin is Atorvastatin (ATV), this amount can be comprised between 5 µg and 200 µg per mg of particle or microsphere. This amount will most likely be between 20 µg and 1000 µg per mg of particle or microsphere in case the drug is paclitaxel.

Atorvastatin (ATV) inhibits expansive remodeling and IH in arterialized vein graft by limiting the macrophage infiltration and reducing the tissue proteolytic activity [18]. The application of ATV in the perivascular area may inhibit the hVSMCs migration and the myofibroblast present in the adventitia. Although statins are traditionally thought to exert their beneficial effects on saphenous vein graft patency through lipid lowering, there are clinical data suggesting additional mechanisms involved. Analysis of the POST-coronary artery bypass surgery trial population revealed a significant protective effect of intensive vs. moderate statin treatment on incidence of saphenous vein graft restenosis, independently of LDL lowering [19]. Treatment of isolated human venous hVSMCs to proliferate, through mevalonate-reversible mechanism [20] and suppressed the formation of vein graft IH [21]. Statins exert their effects through inhibition of 3-hydroxy-3-methylglutaryl-coenzyme A (HMG-CoA) reductase by blocking substrate binding to the active site of the enzyme.

In a preferred embodiment, the at least one rapidly delivered compound effective on the acute inflammatory phase of the early stage of restenosis development will be aspirin and the at least one compound effective on later phases of restenosis development will be atorvastatin.

The term "pharmaceutically acceptable salt" refers to salt of, for example, a statin of the invention. Examples of such salts include, but are not restricted, to base addition salts formed by reaction with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-I,2-ethanediamine, tromethamine, ethanolamine, diethanolamine, ethylenediamine, N-methylmorpholine, procaine, piperidine, piperazine and the like are contemplated being within the scope of the instant invention.

In case the at least one compound effective on later phases of restenosis development is a mitotic inhibitor, then it will be selected from the non-limiting group comprising paclitaxel, sirolimus, c-myc antisense c-fos+c-jun antisense, PCNA antisense, NF kappa B decoy, and E2F decoy, or a combination of two or more thereof. Preferably, the at least one compound effective on later phases of restenosis development is paclitaxel, or a derivative thereof such as, e.g. DHA-paclitaxel or PG-paclitaxel.

The compound effective on later phases of restenosis development and compound effective on the acute inflammatory phase of the early stage of restenosis development are both present in the pharmaceutical composition of the invention in a therapeutically effective amount. As used herein, a "therapeutically effective amount" is an amount effective, and also safe, to reduce and/or prevent restenosis development.

As used throughout the specification, a "subject in need thereof" refers to mammalian patient, and most preferably a human patient, who is suffering from restenosis or at risk of developing restenosis at risk of suffering from restenosis recurrence.

Typically, subjects at risk of restenosis include those having or expected to have open surgical revascularization.

Pharmaceutical formulations of the invention may further comprise one or more pharmaceutically acceptable additional ingredient(s), such as alum, stabilizers, antimicrobial agents, buffers, coloring agents, adjuvants, and the like. The compounds of the invention, together with a conventionally employed adjuvant, carrier, diluent or excipient may be placed into gel phase as described herein.

The present invention also relates to a method of treatment and/or prevention of restenosis in a subject in need thereof, said method comprising administering a pharmaceutical formulation consisting in a gel phase comprising i) at least one rapidly delivered compound effective on the acute inflammatory phase, or any active metabolite of said at least one compound, and ii) a sustained release formulation comprising at least one compound effective on later phases of restenosis development.

Preferably, the sustained release formulation sustains a controlled and stable release of the at least one compound effective on later phases of restenosis development for a time sufficient to prevent the development of restenosis. Usually, this time is comprised between up to 2 to up to 8 weeks, preferably between up to 3 to up to 6 weeks, and most preferably this time is up to 4 weeks.

As use herein, 'rapidly delivered' refers to a time frame lasting from 1 h up to 7 days, mostly preferred up to 3 days, or mostly preferred up to 4 days.

"Administering", as it applies in the present invention, refers to contact of a pharmaceutical formulation, usually in the form of a therapeutically effective amount, to a subject in need thereof, preferably a mammal, most preferably a human.

Also envisioned in the present invention is a kit for the treatment and/or prevention of restenosis comprising a pharmaceutical formulation for use in the treatment and/or prevention of restenosis in a subject in need thereof, said pharmaceutical formulation consisting in a gel phase comprising i) at least one rapidly delivered compound effective on the acute inflammatory phase, or any active metabolite of said at least one compound, and ii) a sustained release formulation comprising at least one compound, or any active metabolite of said at least one compound, effective on later phases of restenosis development.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

Atorvastatin (ATV)-Loaded Hydrogel

Preparation of ATV Incorporated in the Hydrogel

Hyaluronic acid gels (Fortelis Extra®, Anteis, CH), consist of 25.5 mg/ml cross-linked hyaluronic acid obtained from biofermentation suspended in a phosphate buffer. Calcium ATV obtained from Chemos GmbH (Regenstauf, Germany) was dissolved in 33% ethanol aqueous solutions and incorporated in the hydrogel at the desired concentration. The hydrogel was then lyophilized. Sterile water was then added to acquire their initial volume and were left to rehydrate for a period of 24 h.

In Vitro Release Kinetics of ATV Incorporated in the Hydrogel

To study the release kinetic profile from ATV incorporated in the hydrogel, the gels were placed on the bottom of wells in 24-wells cell culture plates and separated from the medium by a dialysis membrane (cutoff: 14 kDa). The medium was regularly sampled to assess the amount of ATV by HPLC.

Figure 1:
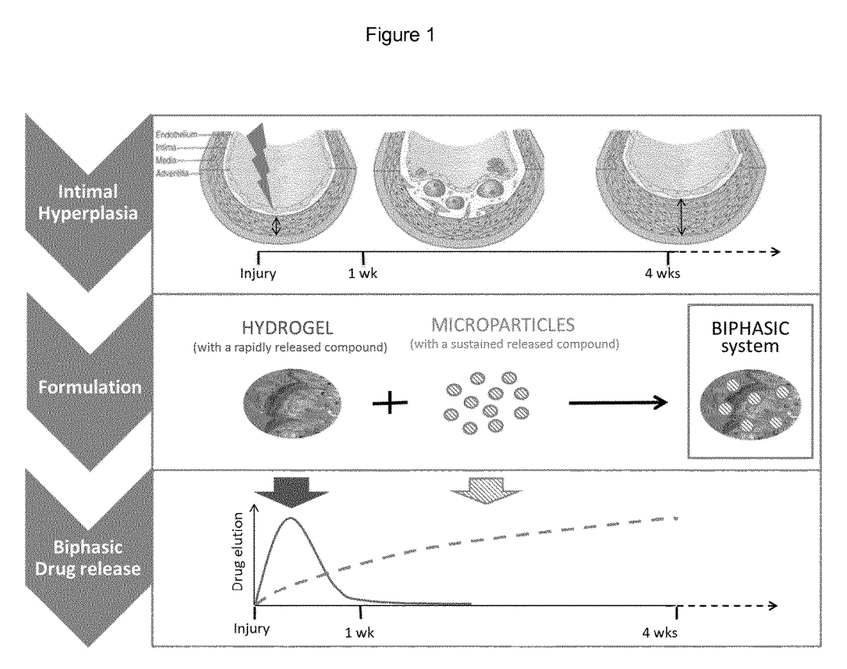
Figure 2:
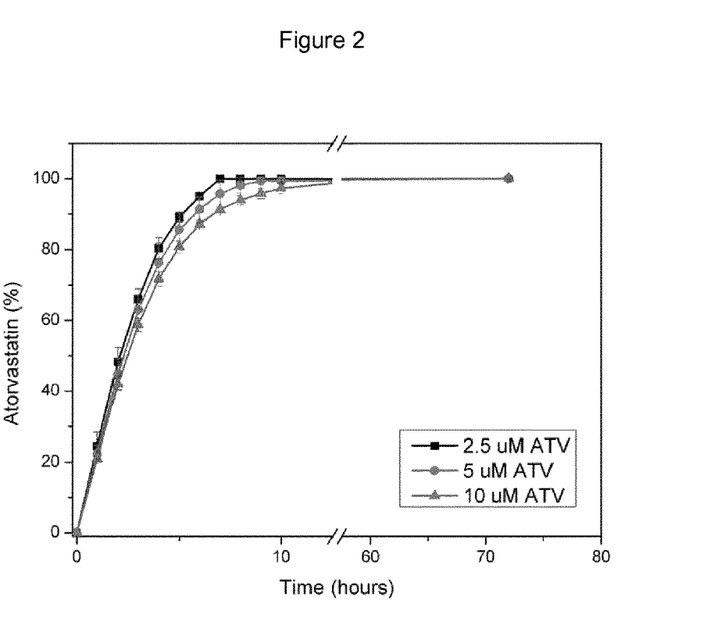
FIG. 2: Release kinetic from the hydrogels incorporating ATV. Different amounts of Atorvastatin (ATV) were incorporated in the hydrogel (2.5 µM, 5 µM, 10 µM). For all samples, ATV was released within 12 hours from the hydrogel. The retention effect of the hydrogel was negligible. No significant differences (t-test, p>0.05) among release profiles were observed between the three different concentrations.
Figure 3:
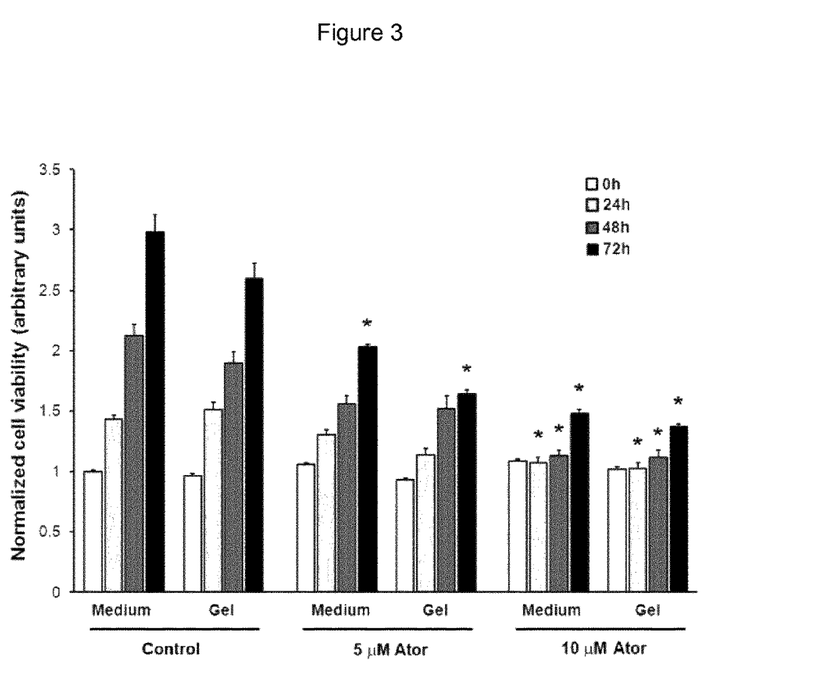
FIG. 3: ATV released from the hydrogel decreased viability of human vascular smooth muscle cells (hVSMC). The viability of hVSMCs, as assessed by the MTT test, was significantly reduced by 5-10 µM ATV, whether the drug was added directly to the culture medium (Medium) or was released by a hydrogel (Gel). This change was faster (24 h) in the presence of 10 µM than 5 µM ATV (72 h)*P<0.05, versus the respective cells incubated in absence of ATV (control).
Figure 4:
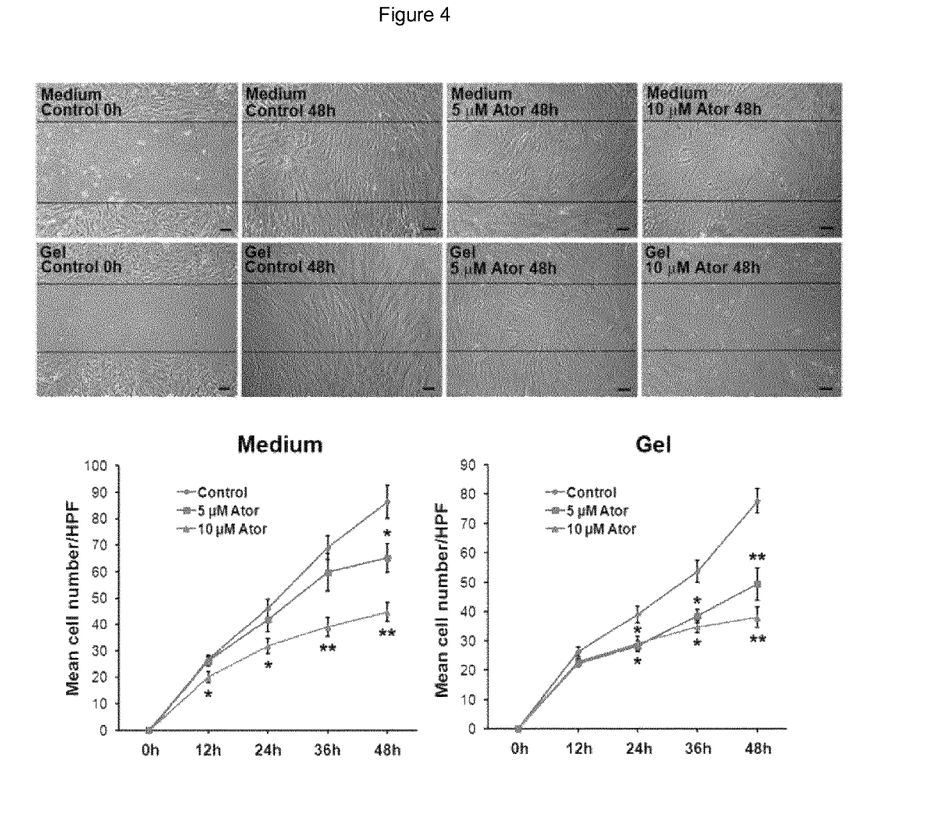
Figure 5:
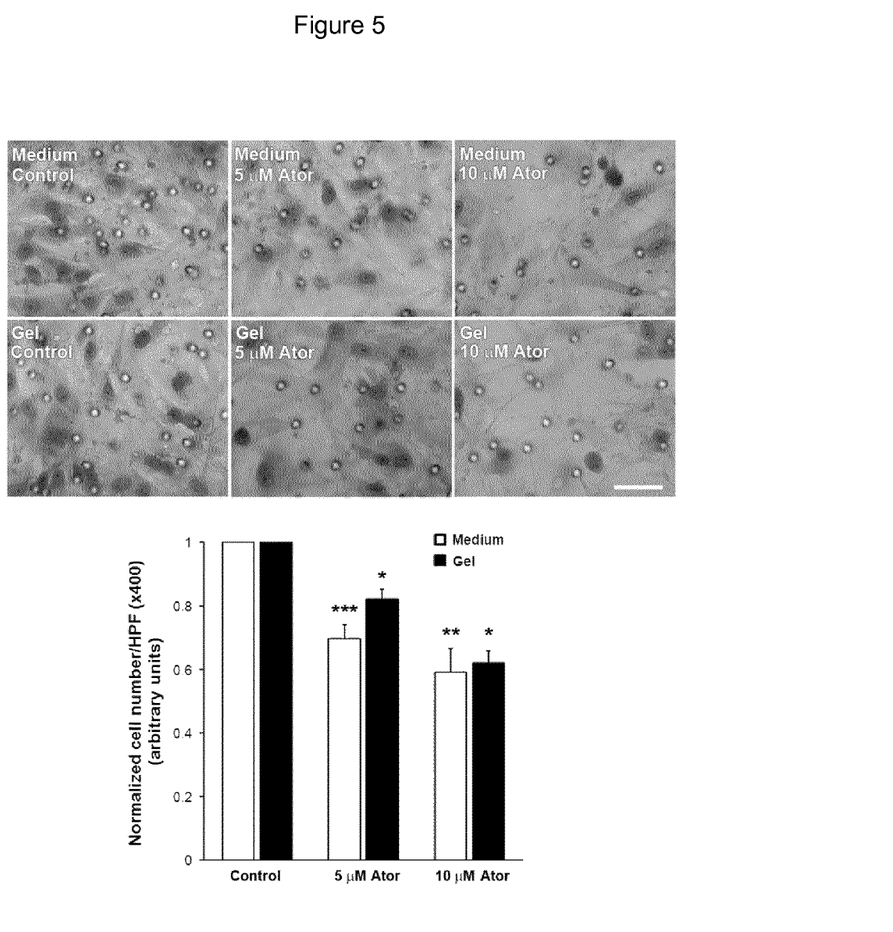
Figure 6:
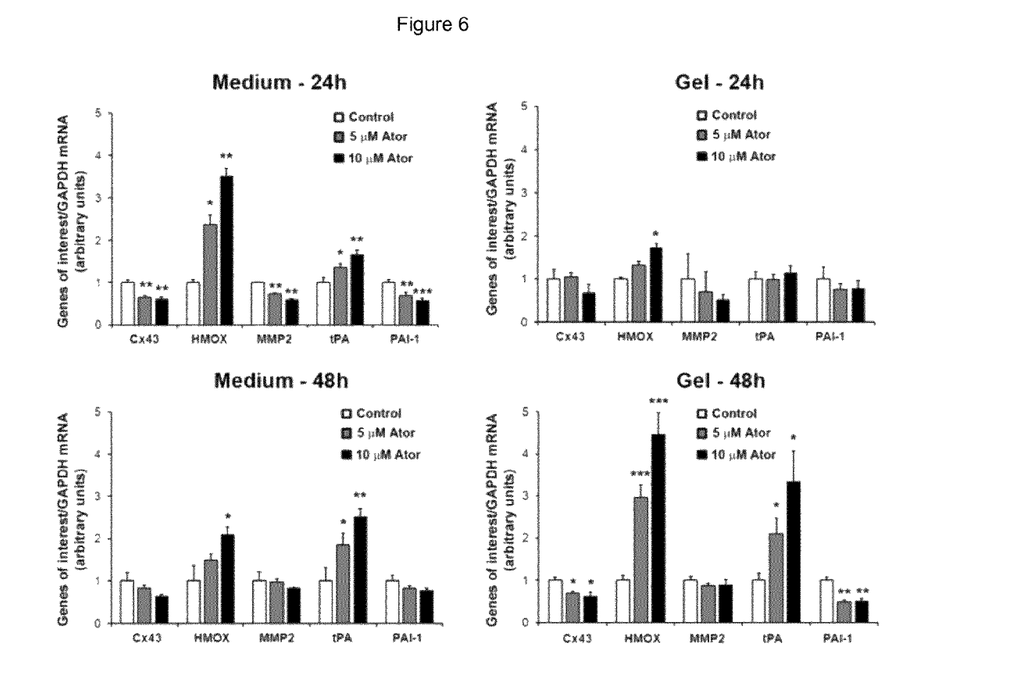

When loaded in hydrogels, ATV is rapidly released with 100% release after 12 h and the release kinetics show a similar pattern independently of the concentration (FIG. 2).

In Vitro Evaluation of the Atorvastatin Activity Once Incorporated in the Hydrogel, on Cell Cultures ATV incorporated in the hydrogels were assayed on primary human vascular smooth muscle cells (hVSMC) to test cell viability and accordingly whether ATV is released from the hydrogels in its active form. To that end, experiments on the influence of the drug on migration and transmigration of the hVSMC and the expression of different mRNAs of proteins involved in the cellular invasivity were performed.

As shown in FIGS. 3-6, atorvastatin incorporated in the hydrogel has functional effects on HSVC. The magnitude of the effect is dose dependent and related to the effect of the native drug in solution.

Overall, using primary hSVMC culture at passage 2-5, we demonstrated that ATV decreased viability and proliferation as well as transmigration of human SMC and differently regulates the expression of genes involved in the development of IH. Quantitative assessment of smooth muscle cells mRNA levels from human veins in presence of atorvastatin shows decreased PAI-1 and MMP2 whereas tPA and the heme oxygenase (HMOX) were increased.

In summary, in vitro cell assays have shown that ATV is released in an active form from the hydrogels. Dose dependent efficacy was demonstrated and some significant differences were recorded when comparing ATV in solution or in a gel, even showing increased activity in the presence of the gel.

Example 2

ATV-Loaded in Microspheres Incorporated in the Hydrogel

Preparation of ATV-Loaded Microspheres

Figure 7:
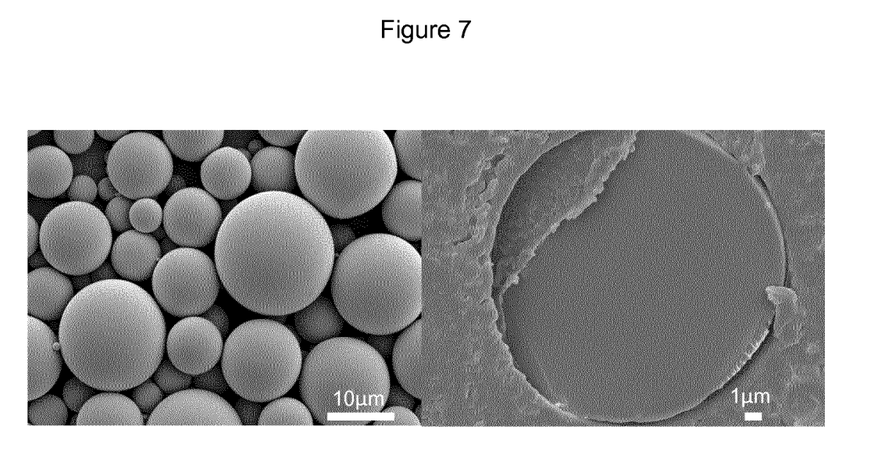
FIG. 7: Scanning electron photomicrographs of the atorvastatin loaded PLGA microspheres and their section. Microspheres are spherical, smooth with an average size of 10 µm (left panel), with a solid internal structure (right panel).

ATV-loaded microspheres were prepared according to an emulsification-evaporation process. The polymer used was the poly lactic co glycolic acid polymers (MW: 20 kDa, Resomer RG502, Boehringer-Ingelheim). A solution of Resomer RG502 and ATV was prepared in methylene chloride and vigorously mixed with an aqueous solution of polyvinyl alcohol. The emulsion was then added in a large volume of water and the solvent was left to evaporate at room temperature overnight. Particles were washed and concentrated by successive steps of centrifugation/resuspension before freeze-drying. Particles were characterized for size, morphology and ATV loading efficiency was determined by a HPLC method (FIG. 7).

This process led to the preparation of particles with a mean size of 10 µm loaded with 50 µg ATV/mg of particles.
ATV-Loaded Microspheres and/or Incorporated in the Hydrogel Preparation of the formulation has been run with commercially available hydrogels made of hyaluronic acid (Fortelis extra, Anteis, CH) Gels loaded with 1 mg ATV per ml of gel were obtained. Sterile procedure was set up to provide gel and microspheres for in vitro and in vivo assays. Drug free gels and particles were also prepared for control.

As mentioned previously, ATV was incorporated in the gel as a hydro-alcoholic solution. Particles were put in suspension and incorporated in the hydrogel by gentle mixing. The gels were freeze-dried and subsequently rehydrated with water before use.

Three different formulations were prepared for in vitro and in vivo tests: i) hydrogels containing free ATV and drug free microspheres (G+M−), ii) hydrogels containing ATV encapsulated in microspheres (G−M+), iii) hydrogels containing both free ATV and ATV encapsulated in microspheres (G+M+).
In Vitro Release Profiles of ATV-Loaded Microspheres and/or Free ATV Incorporated in the Hydrogel The release kinetics from particle loaded gels was studied using a modified Franz's cells design. Briefly, the donor chamber were the gels were placed, is separated from the receptor chamber by a synthetic membrane with pores of 0.22 µm allowing the permeation of ATV but not the particles nor of the gel. The receptor compartment was filled with PBS/SDS 0.1% and sampled at given times to determine ATV concentration by HPLC.

Figure 8:
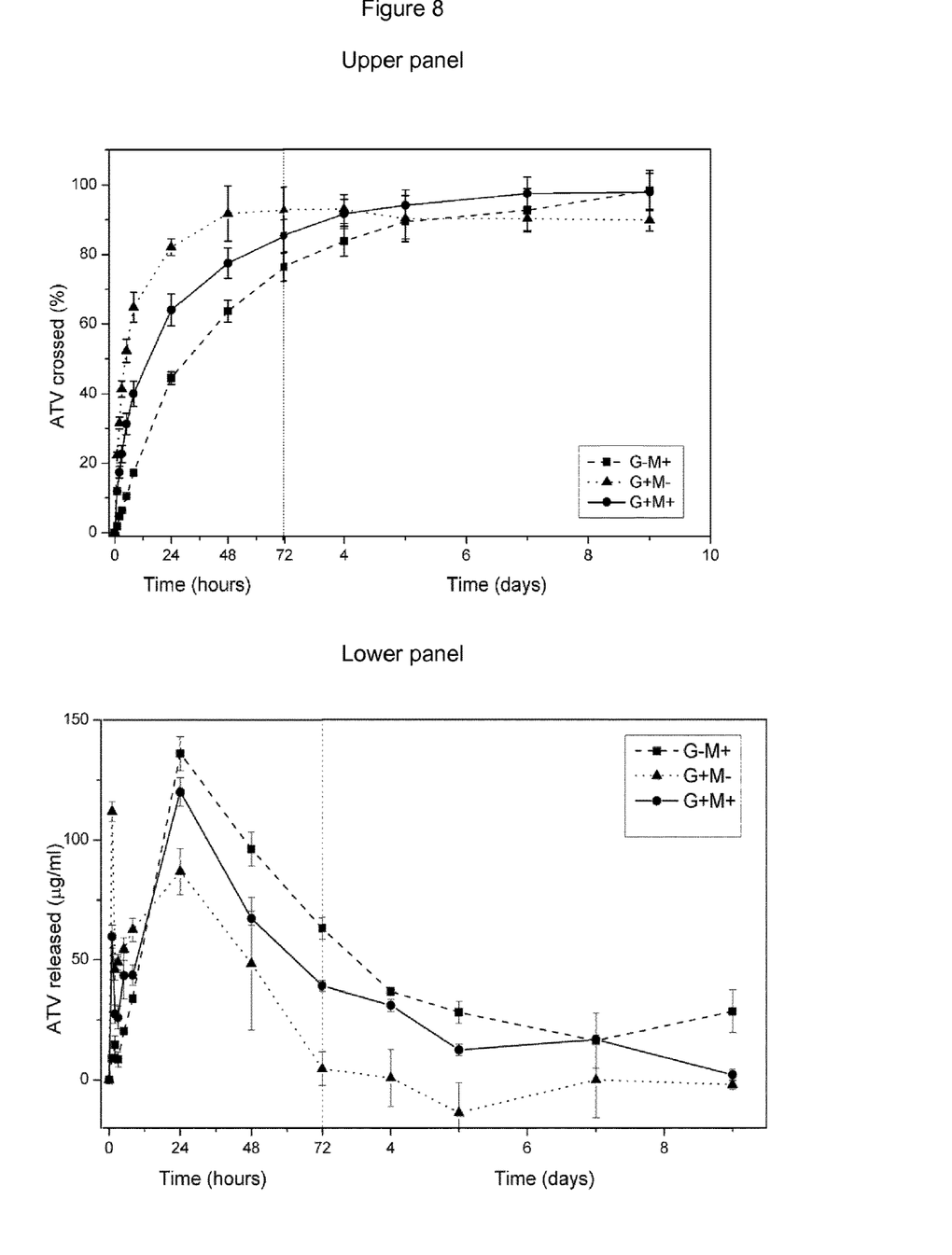
FIG. 8: Cumulative (upper panel) and non-cumulative (lower panel) release of ATV from ATV loaded in microspheres and/or free ATV incorporated in a gel. The total quantity of ATV in the formulations was kept constant at 1 mg/ml by adjusting particles and gel loading. Nomenclature: G−M+: ATV loaded microspheres incorporated in the hydrogel, G+M−: free ATV and drug free microspheres incorporated in the hydrogel, G+M+: free ATV and ATV loaded microspheres incorporated in the hydrogel. The presence of microspheres encapsulating atorvastatin significantly retarded the release from the formulation.
Figure 9:
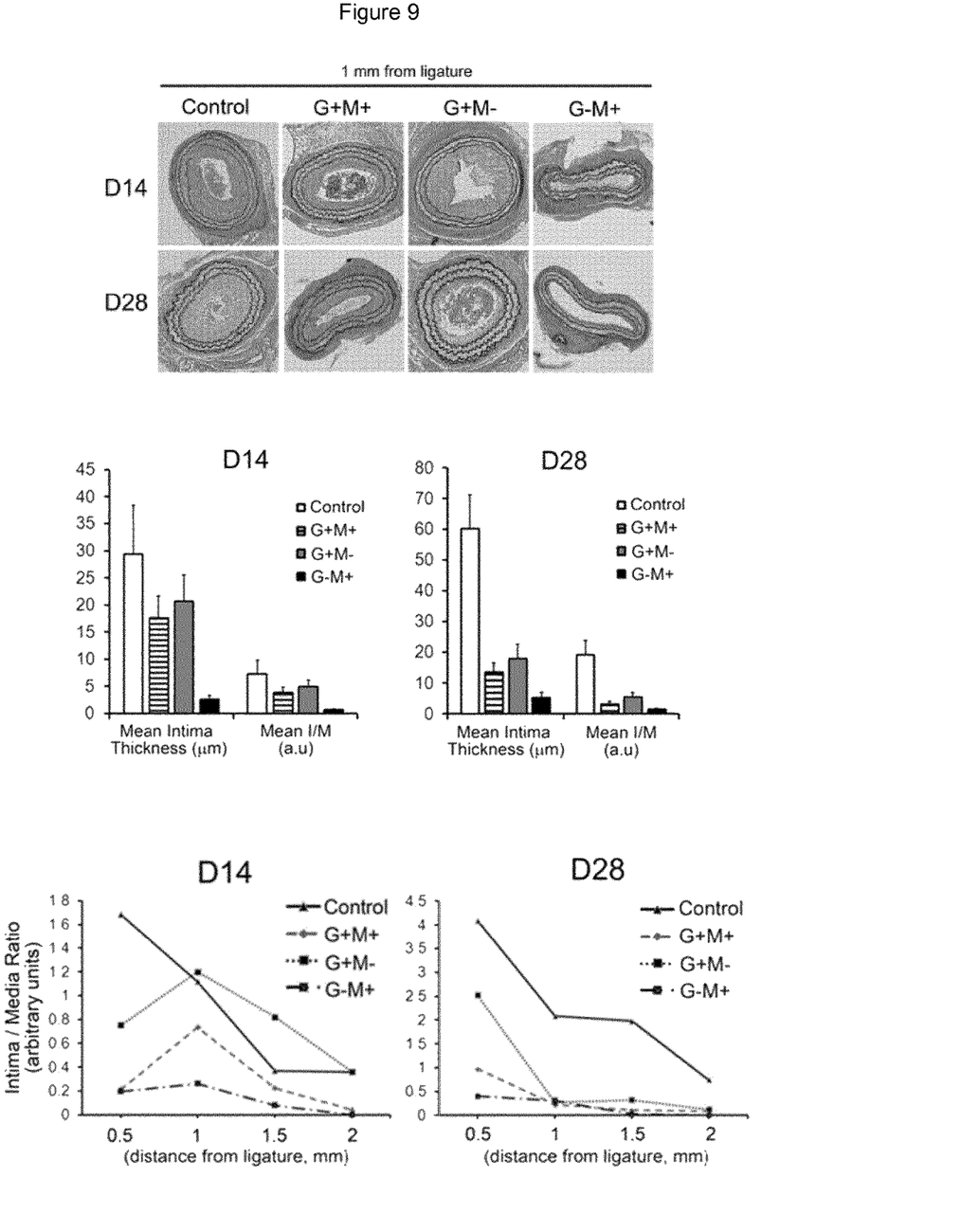

When particles are added to the gel, the ATV release is sustained over a period of time of 8 days, with a peak concentration between 24 and 32 hours depending on the formulation. The release is sustained longer when only loaded-particles (G−M+) are incorporated in the hydrogel. A smoothing effect on the burst usually observed with particle formulations is demonstrated with G+M+, due to the presence of free ATV. No actual lag time is observed in the release of the drug and the formulation is emptied faster than expected (FIG. 8).
In Vivo Mice Carotid Ligation Model C57BL/6 mice (2 to 3 months old) were anesthetized and the left common carotid artery was dissected through a small cervicotomy and ligated near the carotid bifurcation (mouse care, surgery and euthanasia procedures were approved by our institution and the Veterinary Office Lausanne, Switzerland and conforms with the guide for the care and use of laboratory animals, University of Lausanne, A5552-0. Animal authorization 2523). Preliminary experiments performed on WT demonstrated that all animals recovered and showed no symptom of a stroke. At 14 and 28 days after CAL, the intima thickness was increased in the hypertensive animals compared to their respective normotensive WT animals. This model was used to test the efficacy of the ATV-loaded formulations (G−M+: drug free gel with loaded microspheres, G+M−: loaded gel with drug free microspheres, G+M+: loaded gel with loaded microspheres). Fifty microliters of each preparation were applied around the carotid after ligation. No abnormal behavior, no weight loss was observed in the treated animals. The animals were euthanized at D14 and D28 after the surgery. The presence of the gels 28 days after application was also observed. Arteries were collected and processed for histological examination. Histomorphometry was also performed to evaluate the thickness of the different anatomical components of the vessel (FIG. 9).

The most efficient formulation was shown turned out to be the G−M+ demonstrating practically no IH both after 14 and 28 days.

Example 3

Improving ATV-Microspheres Formulation

Microspheres releasing ATV within a longer time frame that follows the development of IH were considered. They were also prepared as well by the emulsion-evaporation technique, as described above, only that this time Resomer RG503 (MW: 42 kD, Boehringer-Ingelheim) was used as a poly-Lactic-co-Glycolic acid. The microspheres generated had a mean average diameter of 20 µm and contained 14 µg ATV per mg of particles.

Figure 10:
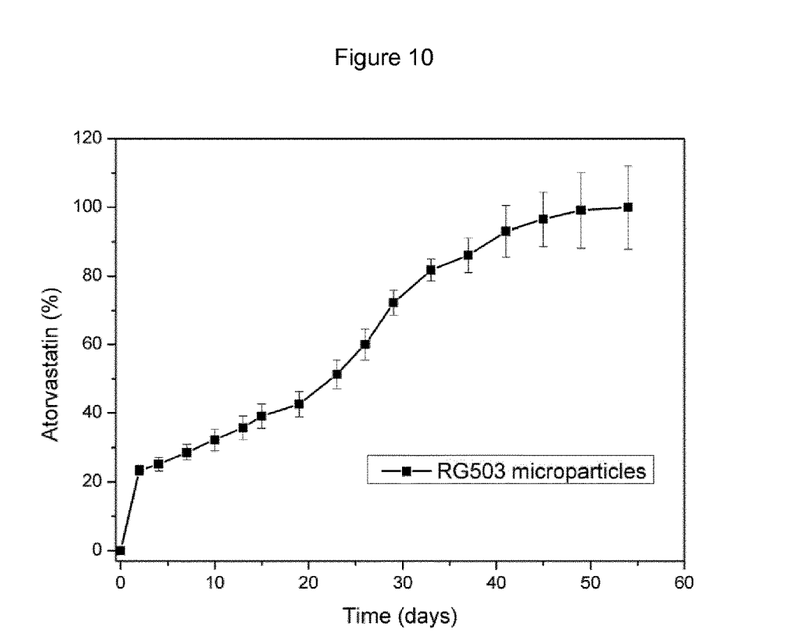
FIG. 10: Extended release kinetics of ATV from ATV loaded microspheres. This batch of microspheres was prepared with poly(D,L-lactide-co-glycolide) (Resomer RG503). The release is sustained for up to 52 days.

50 mg of microspheres were incubated in 50 ml of PBS (pH 7.4)/SDS 0.1%, at 37° C. under gentle agitation. The release profile demonstrated a slight burst within the first 24 hours and ensured a sustained release of the drug for up to 52 days (FIG. 10).

Example 4

ATV Loaded Microspheres and Free ASA Incorporated in the Hydrogel

Preparation of ATV Loaded Microspheres and Free ASA Incorporated in the Hydrogel Preparation of the formulation has been run with commercially available hyaluronic acid hydrogel (Fortelis Extra®, Anteis, Plan-les-Ouates, CH). The ATV loaded microspheres preparation has been described in example 3. An aspirin (Sigma-Aldrich Chemie GmbH, DE) solution in water was prepared and incorporated along with a suspension of ATV microparticles in the hydrogel, at the desired concentration by gentle stirring. The hydrogel was then lyophilized. Sterile water was subsequently added to acquire the initial volume and were left to rehydrate for a period of 24 h.

The prepared formulations contained 400 µg of ASA per ml of hydrogel and 1 mg of ATV encapsulated in the microspheres per ml of hydrogel.
In Vitro Release Kinetics of ATV Loaded Microspheres and Free ASA Incorporated in the Hydrogel The release kinetics of the formulation was studied using a modified Franz cell as described in example 2. The receptor compartment was sampled at given times to determine simultaneously ATV and ASA concentrations by UHPLC.

Figure 11:
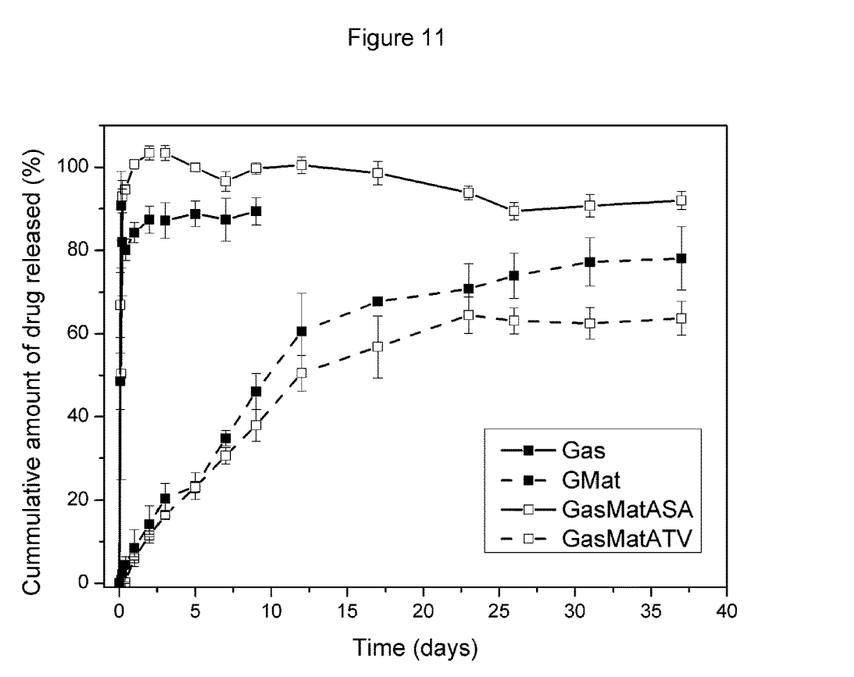
FIG. 11: Release kinetics of ATV and aspirin (ASA) from ATV loaded microspheres and free ASA incorporated in a hydrogel. The gel contained 400 μg of ASA per ml of hydrogel and 1 mg of ATV encapsulated in the microspheres per ml of hydrogel. Nomenclature: Gas: Free ASA incorporated in the hydrogel, GMat: ATV loaded microspheres incorporated in the hydrogel, GasMatASA: Free ASA and ATV loaded microspheres incorporated in the hydrogel, results for ASA, GasMatATV: Free ASA and ATV loaded microspheres incorporated in the hydrogel, results for ATV. While ASA is rapidly released within 2 days, ATV is still released even after 4 weeks.

Aspirin is release is completed after 4 days. ATV released from the microparticles demonstrates a zero order release kinetics during the first 3 weeks. Thereafter small, but not negligible amounts of drug are released even after 4 weeks (FIG. 11).

Example 5

Figure 12:
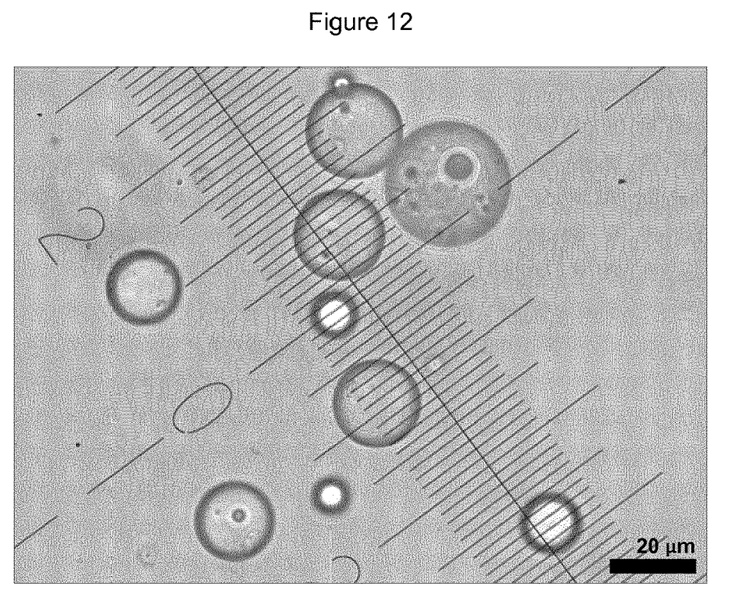
FIG. 12: Light transmission photomicrograph of Paclitaxel (PTX) loaded RG503 microspheres, having an average size of 29 μm.
Figure 13:
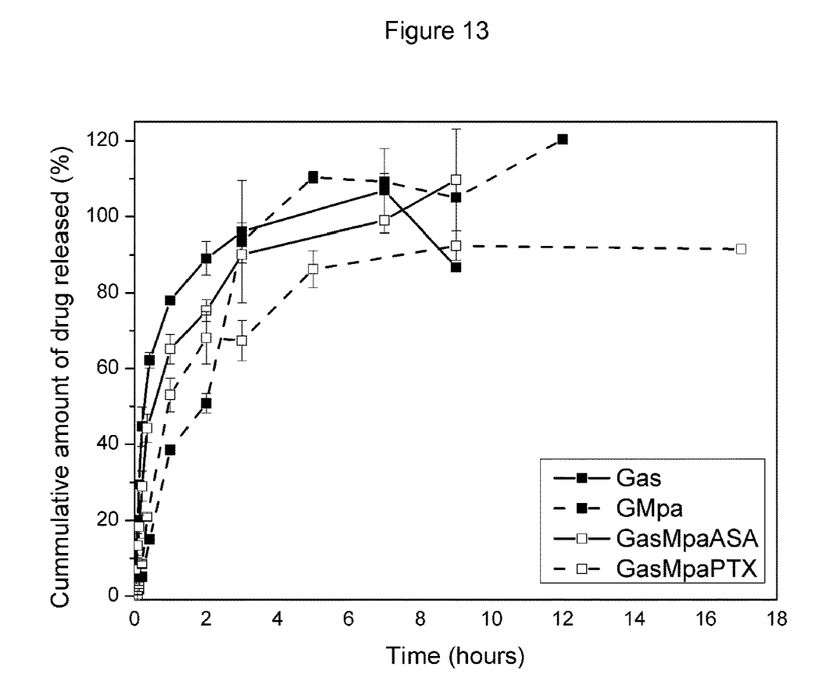
FIG. 13: Release kinetics of PTX and aspirin (ASA) from PTX loaded microspheres and free ASA incorporated in a hydrogel. The gel contained 400 μg of ASA per ml of hydrogel and 4 mg of PTX encapsulated in the microspheres per ml of hydrogel. Nomenclature: Gas: Free ASA incorporated in the hydrogel, GMpa: PTX loaded microspheres incorporated in the hydrogel, GasMpaASA: Free ASA and PTX loaded microspheres incorporated in the hydrogel, results for ASA, GasMpaPTX: Free ASA and PTX loaded microspheres incorporated in the hydrogel, results for PTX. Under these accelerated release conditions ASA is completely released within 4 days and PTX release is sustained for 10 days.

Paclitaxel (PTX) Loaded in Microspheres and Free Aspirin (ASA) Both Incorporated in the Hydrogel Preparation of (PTX) Loaded Microspheres Microspheres encapsulating PTX (Cfm Oskar Tropitzsch GmbH, DE) were prepared by the emulsion evaporation technique described above, using RG503 (MW: 42 kDa, Boehringer-Ingelheim, DE) as a poly-lactic-co-glycolic acid. The microspheres generated were spherical and had a mean average size of 29 μm (FIG. 12). They contained 77 μg of PTX per mg of particles.

Preparation of PTX Loaded Microspheres and Free ASA Incorporated in the Hydrogel Preparation of the formulation has been run with commercially available hyaluronic acid hydrogel (Fortelis Extra®, Anteis, Plan-les-Ouates, CH). An aspirin (Sigma-Aldrich Chemie GmbH, DE) solution in water was prepared and incorporated along with suspension PTX microparticles in the hydrogel, at the desired concentration by gentle stirring. The hydrogel was then lyophilized. Sterile water was subsequently added to acquire the initial volume and was left to rehydrate for a period of 24 h.

The prepared formulations contained 400 μg of ASA per ml of hydrogel and 4 mg of PTX encapsulated in the microspheres per ml of hydrogel.

In Vitro Release Kinetics of PTX Loaded Microspheres and Free ASA Incorporated in the Hydrogel The release kinetics of the formulation was studied using a modified Franz cell as described in example 2 with some modifications. To ensure PTX solubility in the receptor medium, PBS/SDS was replaced by DENA in PBS (0.2M) at a concentration of 2M. This medium provides accelerated release kinetics data, allowing more rapid investigation of long term release formulations. The receptor compartment was sampled at given times to determine simultaneously PTX and ASA concentrations by UHPLC.

Aspirin is released after 4 days, while PTX release is completed only after 10 days. Under these accelerated release conditions, results suggest that the release could be maintained over longer time periods in physiological conditions.

REFERENCES

1. Wiedemann, D., et al., *Perivascular administration of drugs and genes as a means of reducing vein graft failure.* Curr Opin Pharmacol, 2012. 12(2): p. 203-16.
2. Zalewski, A., Y. Shi, and A. G. Johnson, *Diverse origin of intimal cells: smooth muscle cells, myofibroblasts, fibroblasts, and beyond?* Circ Res, 2002. 91(8): p. 652-5.
3. Davies, M. G. and P. O. Hagen, *Pathophysiology of vein graft failure: a review.* Eur J Vasc Endovasc Surg, 1995. 9(1): p. 7-18.
4. West, N., et al., *Enhanced superoxide production in experimental venous bypass graft intimal hyperplasia: role of NAD(P)H oxidase.* Arterioscler Thromb Vasc Biol, 2001. 21(2): p. 189-94.
5. Newby, A. C., *Molecular and cell biology of native coronary and vein-graft atherosclerosis: regulation of plaque stability and vessel-wall remodelling by growth factors and cell-extracellular matrix interactions.* Coron Artery Dis, 1997. 8(3-4): p. 213-24.
6. Thatte, H. S. and S. F. Khuri, *The coronary artery bypass conduit: I. Intraoperative endothelial injury and its implication on graft patency.* Ann Thorac Surg, 2001. 72(6): p. S2245-52; discussion S2267-70.
7. Dobrin, P. B., et al., *Pre-vs postoperative pharmacologic inhibition of platelets: effect on intimal hyperplasia in canine autogenous vein grafts.* J Cardiovasc Surg (Torino), 1992. 33(6): p. 705-9.
8. Dobrin, P. B., F. N. Littooy, and E. D. Endean, *Mechanical factors predisposing to intimal hyperplasia and medial thickening in autogenous vein grafts.* Surgery, 1989. 105(3): p. 393-400.
9. Dobrin, P. B., et al., *Mechanical and histologic changes in canine vein grafts.* J Surg Res, 1988. 44(3): p. 259-65.
10. Owens, G. K., M. S. Kumar, and B. R. Wamhoff, *Molecular regulation of vascular smooth muscle cell differentiation in development and disease.* Physiol Rev, 2004. 84(3): p. 767-801.
11. Jeremy, J. Y., et al., *On the biology of saphenous vein grafts fitted with external synthetic sheaths and stents.* Biomaterials, 2007. 28(6): p. 895-908.
12. Gangadharan, S. P., et al., *Monocyte adhesion to balloon-injured arteries: the influence of endothelial cell seeding.* J Vasc Surg, 2001. 33(6): p. 1247-54.
13. Segel, G. B., M. W. Halterman, and M. A. Lichtman, *The paradox of the neutrophil's role in tissue injury.* J Leukoc Biol, 2011. 89(3): p. 359-72.
14. Channon, K. M. and T. J. Guzik, *Mechanisms of superoxide production in human blood vessels: relationship to endothelial dysfunction, clinical and genetic risk factors.* J Physiol Pharmacol, 2002. 53(4 Pt 1): p. 515-24.
15. Cherepanova, O. A., et al., *Oxidized phospholipids induce type VIII collagen expression and vascular smooth muscle cell migration.* Circ Res, 2009. 104(5): p. 609-18.
16. George, S. J., et al., *Sustained reduction of vein graft neointima formation by ex vivo TIMP-3 gene therapy.* Circulation, 2011. 124(11 Suppl): p. S135-42.
17. Edelman, E. R., M. A. Nugent, and M. J. Karnovsky, *Perivascular and intravenous administration of basic fibroblast growth factor: vascular and solid organ deposition.* Proc Natl Acad Sci USA, 1993. 90(4): p. 1513-7.
18. Qiang, B., et al., *Statin therapy prevents expansive remodeling in venous bypass grafts.* Atherosclerosis, 2012. 223(1): p. 106-13.
19. Domanski, M., et al., *Pleiotropic effect of lovastatin, with and without cholestyramine, in the post coronary artery bypass graft (Post CABG) trial.* Am J Cardiol, 2008. 102(8): p. 1023-7.
20. Yang, Z., et al., *HMG-CoA reductase inhibition improves endothelial cell function and inhibits smooth muscle cell proliferation in human saphenous veins.* J Am Coll Cardiol, 2000. 36(5): p. 1691-7.
21. Yamanouchi, D., et al., *Hydrophilic statin suppresses vein graft intimal hyperplasia via endothelial cell-tropic Rho-kinase inhibition.* J Vasc Surg, 2005. 42(4): p. 757-64.

The invention claimed is:
1. A method of treatment of restenosis after open surgical revascularization in a subject in need thereof, said method comprising administering by the perivascular route a pharmaceutical formulation consisting in a gel phase comprising i) at least one rapidly delivered compound effective on the acute inflammatory phase of the early stage of restenosis development comprising a statin, and ii) a sustained release formulation comprising a statin effective on later phases of restenosis development, wherein the sustained release formulation is in the form of microspheres or nanospheres.

2. The method of treatment of restenosis of claim 1, wherein the microspheres or nanospheres are made of a biocompatible, biodegradable polymer.

3. The method of treatment of restenosis of claim 2, wherein the biocompatible, biodegradable polymer is selected from the group consisting of a polylactide, a copolymer of a polylactide, a polyglycolide, a copolymer of a polyglycolide, a poly(lactide-co-glycolide) copolymer, a polylactic acid, a copolymer of a polylactic acid, a polyglycolic acid, a copolymer of a polyglycolic acid, a poly(lactic acid-co-glycolic acid) copolymer, a polycaprolactone, a copolymer of a polycaprolactone, a polycarbonate, a copolymer of a polycarbonate, a polyesteramide, a copolymer of a polyesteramide, a polyanhydride, a copolymer of a polyanhydride, a polyamino acid, a copolymer of a polyamino acid, a polyorthoester, a copolymer of a polyorthoester, a polycyanoacrylate, a copolymer of a polycyanoacrylate, a poly(p-dioxanone), a copolymer of a poly(p-dioxanone), a polyalkylene oxalate, a copolymer of a polyalkylene oxalate, and a combination of two or more thereof.

4. The method of treatment of restenosis of claim 1, wherein the gel is a hydrogel.

5. The method of treatment of restenosis of claim 4, wherein the hydrogel is based on hyaluronic acid, or one of its salts.

6. The method of treatment of restenosis of claim 5, wherein the hyaluronic acid, or one of its salts, is cross-linked.

7. The method of treatment of restenosis of claim 1, wherein the statin effective on later phases of restenosis development is selected from the group consisting of atorvastatin, fluvastatin, pravastatin, pitavastatin, lovastatin and simvastatin, and a combination of two or more thereof.

8. The method of treatment of restenosis of claim 1, wherein the at least one rapidly delivered compound is released in a time frame from 1 hour to 7 days and the statin of the sustained release formulation is released during a time of up to 8 weeks.

9. The method of treatment of restenosis of claim 1, wherein the amount of statin present in the microspheres or nanospheres is between 5 µg and 200 µg per mg of microsphere or nanosphere.

* * * * *